United States Patent [19]

Dorsey et al.

[11] Patent Number: 5,358,497
[45] Date of Patent: Oct. 25, 1994

[54] MEDICAL LOCKING DEVICE

[75] Inventors: Denis P. Dorsey, Levittown; Shih-Mei Wu, Newtown, both of Pa.

[73] Assignee: Bioteque America, Inc., Langhorne, Pa.

[21] Appl. No.: 179,948

[22] Filed: Jan. 11, 1994

[51] Int. Cl.$^5$ .............................................. A61M 5/315
[52] U.S. Cl. .................................................. 604/220
[58] Field of Search .................. 604/110, 187, 218, 220

[56] References Cited

U.S. PATENT DOCUMENTS

| | | |
|---|---|---|
| 3,890,971 | 6/1975 | Leeson et al. . |
| 4,386,606 | 6/1983 | Tretinyak et al. . |
| 4,610,672 | 9/1986 | Ewalt et al. . |
| 4,711,637 | 12/1987 | Leigh et al. ........................ 604/220 |
| 4,758,232 | 7/1988 | Chak .................................. 604/220 |
| 4,874,385 | 10/1989 | Moran et al. . |
| 4,890,626 | 1/1990 | Wang . |

*Primary Examiner*—John D. Yasko
*Attorney, Agent, or Firm*—Dennison, Meserole, Pollack & Scheiner

[57] ABSTRACT

A medical locking device securely fits onto finger grips of a syringe. The locking device is axially aligned with the syringe along a defined longitudinal axis wherein the syringe receives a plunger. The locking device includes a centrally positioned aperture which receives the shaft of the plunger. A retaining member is positioned around the aperture and receives the finger grips of the syringe by engaging at least three sides of the finger grips. This eliminates shifting of the medical locking device and there are opposed cutting members which are chordally positioned in the aperture. The cutting members taper as fine cutting edges for wedging into the plunger during execution of a locking position. To utilize the device, the user twists the plunger into a locking position so that the cutting members wedge into the plunger. This locking position eliminates and prevents any further plunger movement in either direction along the longitudinal axis.

11 Claims, 1 Drawing Sheet

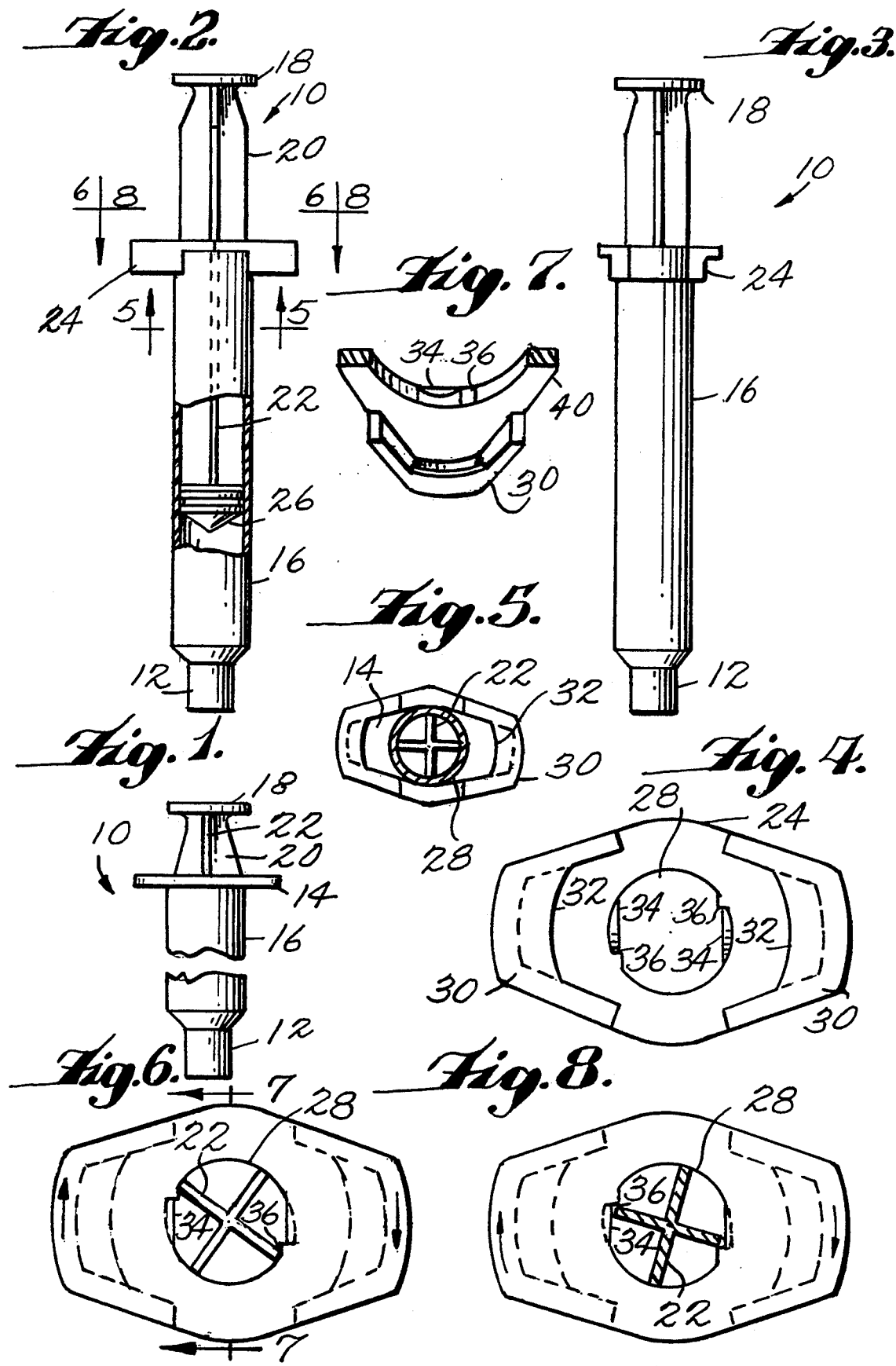

MEDICAL LOCKING DEVICE

BACKGROUND OF THE INVENTION

Field of the Invention

This invention relates to medical syringes. More specifically, the invention is directed to a locking device having a winged retaining member which completely engages all sides of finger grips on the syringe.

There are many devices developed to lock a movable plunger of a syringe in a certain position so that the syringe can be controlled. For example, U.S. Pat. No. 3,890,971 to Lesson et al. describes an one-time syringe having a permanently locking plunger by dents to prevent reuse. U.S. Pat. No. 4,386,606 to Tretinyak et al. discloses a syringe with a barrel and plunger. The plunger is removable along the axis of the barrel and lockable by a locking means. The locking means includes a cam member which when moved into a position forces the plunger into binding contact with the barrel. U.S. Pat. No. 4,610,672 to Ewalt et al. describes a locking device attached to the finger grips of a syringe and includes an aperture aligned with the longitudinal axis of the barrel. The aperture includes two ridges extending chordally across the circular opening wherein the ridges engage the plunger when oriented in one position. U.S. Pat. No. 4,874,385 to Moran et al. describes a movable locking member which is capable of moving axially on the plunger and can be placed in a fixed condition to limit movement of the plunger. U.S. Pat. No. 4,890,626 to Wang discusses a syringe plunger stop and lock attachment wherein the plunger is specifically designed with grooves at predetermined distances such that the stop member will engage the plunger and prevent axially movement of the plunger.

Each of these stopping or locking devices either require modifications of the plunger or syringe, addition of a separate camming means, or do not securely fit the finger grips of the syringe and thus shift or slide when in use.

Accordingly, the medical locking devices exemplified in the patents referred to hereinabove illustrate the many improvements made over the years in simplifying and improving this aspect of syringes. There still exists, however, in this industry, a need for a medical locking device which absolutely prevents and movement of the plunger as well as shifting of the locking device once locked in a manner that particularly improves the safety, efficiency and economics of the syringes with locking devices, and simplifies installation, operation and maneuverability.

SUMMARY OF THE INVENTION

The present invention is an improvement on the prior art devices because the medical locking device securely fits onto finger grips of a syringe having a longitudinal axis. The locking device is axially aligned with the syringe along the defined longitudinal axis wherein the syringe receives a plunger.

The locking device includes a flat top having a centrally positioned aperture. The aperture receives the shaft of the plunger so the shaft of the plunger freely moves axially through the aperture. A retaining member is positioned around the aperture for securing the locking device onto the finger grips of the syringe by engaging at least three sides of the finger grips. This engagement eliminates shifting of the medical locking device and positively aligns the aperture with the barrel of the syringe.

There are opposed cutting members which are chordally positioned in the aperture and extend in a plane defined by the flat top. The cutting members taper into the aperture as a fine cutting edge for wedging into the plunger during execution of a locking condition. There are at least two stop members diametrically positioned from each other and fixed at opposite ends of the cutting members. Each of the stop members extends the complete thickness of the device from the flat top to the other side of the flat top.

The medical locking device allows the user the freedom to lock the plunger anywhere along the longitudinal axis. After the medical device is securely positioned on the finger grips of the syringe, it completely engages the finger grips and allows the user maneuverability of the plunger. The locking device has a first unlocked position. In this position, the user is free to move the plunger in an axial direction without any interference from the locking device. Next, is the locking position. In this position, the plunger is twisted so that the cutting members wedge into the plunger. This locking eliminates and prevents any further plunger movement in either direction along the longitudinal axis. There is no restriction or limitations as to where the plunger can be locked. Accordingly, the user can control the actuation of the syringe with the locking device.

It is an object of the invention to provide a medical locking device for mounting on finger grips of a syringe having a plunger freely moving axially in and out of a barrel of the syringe.

It is another object of the invention to provide a device with a flat top defining a plane and having an aperture centrally positioned in the plane.

It is an advantage of the invention that the aperture for receiving the plunger is axially aligned with the barrel of the syringe when the device is mounted on the finger grips.

It is another advantage of the invention that there is a pair of retaining members extending perpendicularly from the flat top.

Another object of the invention is that the retaining members completely engage the finger grips on at least three sides of the finger grips to eliminate shifting of the locking device.

A further advantage of the invention is that the retaining members insure proper axis alignment of the centrally positioned aperture with the barrel of the syringe, after engagement.

An object of the invention is to have a pair of diametrically opposed cutters.

Another object of the invention is to have the cutters chordally positioned in the centrally located aperture and extend from the plane of the flat top into the aperture.

A further object is to have the pair of cutters tapering to a cutting edge in the aperture.

Another object is to have a pair of stop members diametrically positioned from each other and fixed at opposite ends of the cutters.

It is an advantage of the invention to include stop members extend from the flat top to the other side of the flat top.

Another advantage of the invention is that the medical locking device securely fits onto the finger grips of the syringe with the aperture axially aligned with the barrel of the syringe for receiving the plunger of the syringe, wherein the plunger can be twisted so that the cutters cut into the plunger for eliminating and preventing further plunger movement in either direction along the axis defined by the plunger in the barrel and the centrally positioned aperture.

Further objects and advantages of the invention will became apparent from a consideration of the drawings and ensuing description of these drawings.

BRIEF DESCRIPTION OF THE DRAWINGS

FIG. 1 illustrates a syringe and plunger without the medical locking device of the present invention;

FIG. 2 illustrates a syringe and plunger with the medical locking device of the present invention;

FIG. 3 illustrates a side view of a syringe and plunger with the medical locking device of the present invention;

FIG. 4 is a bottom view of the medical locking device with the cutting edges and retaining members of the present invention illustrated;

FIG. 5 illustrates a bottom view taken along line 5—5 of FIG. 2 illustrating the syringe and plunger and the medical locking device of the present invention;

FIG. 6 illustrates a top view of the medical locking device in the unlocked position taken along line 68—68 of FIG. 2;

FIG. 7 is a perspective cross sectional view taken along line 7—7 of FIG. 6 illustrating the cutting edge and stop member of the present invention; and FIG. 8 illustrates a top view of the medical locking device of the present invention in the locked position taken along line 68—68 of FIG. 2.

DESCRIPTION OF THE INVENTION

Referring now to the drawings wherein like numerals represent like components, FIG. 1 illustrates a partial view of a common syringe such as a BD 10 mm clear syringe. This syringe 10 includes a syringe tip 12 at the distal end and finger grips 14 at the proximal end. The ends are connected by a syringe body or barrel 16 which is hollow for receiving a plunger 18. The plunger 18 includes a shaft 20 with a plurality of fins or ribs 22 extend the length of the plunger shaft 20 and parallel to an imaginary longitudinal axis.

FIG. 2 illustrates the syringe 10 with the medical locking device 24 of the present invention. The medical locking device 24 securely fits onto the finger grips 14 of the syringe 10 which has the longitudinal axis. The locking device 24 is axially aligned with the syringe 10 along the longitudinal axis to receive the plunger 18 having the plunger ribs or fins 22. In the figure, there is a cut away portion generally illustrating the distal end of the plunger 18 having a rubber plunger tip 26.

FIG. 3 illustrates a side view of the syringe 10 having the medical locking device 24 engaged over the finger grips 14. The figure illustrates the engagement of the device 24 which nearly completely covers the finger grips 18 of the syringe 10.

Referring now to FIG. 4, an enlarged bottom view of the medical locking device 24 is illustrated without the syringe 10. The device 24 comprises a centrally positioned aperture 26. The aperture 28 is as wide as the barrel so that the aperture can receive the shaft 20 of the plunger 18 with the shaft 20 of the plunger 18 capable of freely moving axially through the aperture 28.

On the outer edges of the device 24 are similar looking retaining members 30. The retaining members are designed so that the device 24 can be placed over the finger grips 14 of the syringe 10. The engagement member 32 extends nearly to the aperture 28 so that the retaining member 30 when positioned on the finger grips 14 will almost completely cover the grips on three sides and part of the bottom as well as the top. The retaining members 30 are positioned around the aperture 28 at the outer edges of the device 24 and receive the finger grips 14 of the syringe 10 on at least three sides to eliminating shifting of the medical locking device 24 and positively aligning the centrally positioned aperture 28.

Extending into the aperture are diametrically opposed cutting members 34. The cutting members are chordally positioned in the centrally located aperture 28 and are positioned next to a stop member 36. There are two stop members extending from the circumference of the aperture 28 past the chord of the cutting means 34 and perpendicular to the chord. The stop members 36 are diametrically positioned from each other across the aperture 28.

FIG. 5 illustrates a bottom view of the medical locking device 24 connected to a syringe finger grips 14. As shown in the figure, retaining members 30 engage and cover at least three sides of the finger grips 14 as well as a portion of the bottom surface.

FIG. 6 and FIG. 8 illustrate top views of the medical locking device 24 taken along line 68—68 of FIG. 2. These figures illustrate the locking of the device 24 mounted on a syringe 10 having plunger fins 22. FIG. 6 shows the fins 22 axially aligned in the aperture 28 and free to move through the aperture 28. FIG. 8 illustrates the fins 22 placed in the locked position wherein the fins 22 abut the stop members 36 with the cutting members 34 wedged into the fins 22. Accordingly, the medical locking device 24 is securely positioned on the finger grips 14 of the syringe 10 by the retaining means 30 which completely engage the finger grips 14. As shown in FIG. 8, this allows the plunger 18 to be twisted in a locking position so that the cutting members 34 wedge into the plunger fins 22 which eliminates and prevents any further plunger movement in either direction along the longitudinal axis.

Referring now to FIG. 7, the figure shows a perspective sectional view taking along lines 7—7 of FIG. 6. In this figure, the retaining member 30 is shown, partially. Also, the location of stop member 36 is illustrated. This stop member 36 extends the thickness of the upper portion 40 of the device 24. Additionally, the cutting means 34 is shown. It extends to the stop member 36 and no further.

While the above description contains many specificities, these should not be construed as limitations on the scope of the invention, but rather as exemplification of one preferred embodiment thereof. Many other variations are possible. Accordingly, the scope of the invention should be determined not by the embodiment illustrated, but by the appended claims and their legal equivalents.

We claim:

1. A medical locking device for mounting on finger grips of a syringe having a plunger for freely moving axially in and out of a barrel of the syringe, said locking device comprising:
    a flat top defining a plane and having an aperture centrally positioned in said plane, said aperture for receiving the plunger and being axially aligned with the barrel of the syringe when mounted on the finger grips;

a pair of retaining members extending perpendicularly from said flat top, said retaining members for completely engaging the finger grips on at least three sides to eliminate shifting of the locking device and insure proper axis alignment of said centrally positioned aperture with the barrel of the syringe;

a pair of diametrically opposed cutters, said cutters chordally positioned in said centrally located aperture and extending from the plane of the flat top into the aperture, said pair of cutters tapering to a cutting edge in said aperture;

said medical locking device securely fitting onto the finger grips of the syringe with said aperture axially aligned with the syringe for receiving the plunger of the syringe, wherein the plunger can be twisted so that said cutters cut into the plunger to eliminate and prevent further plunger movement in either direction along the axis defined by the plunger and said centrally positioned aperture; and said locking device further includes a pair of stop members diametrically positioned from each other and fixed at opposite ends of said cutters, each said stop member extending from said flat top to the other side of said flat top.

2. The medical locking device of claim 1, wherein said cutters are tapered so that the edges are directed upwardly to insure downward motion of the plunger is prevented.

3. The medical locking device of claim 1, wherein said cutters occupy two positions, a locked position wherein the plunger is prevented from moving and a unlocked position wherein the plunger is able to be freely moved along the defined axis.

4. The medical locking device of claim 3, wherein the locked position forces the cutting edge to dig into the plunger such that any further downward force on the plunger allows the cutter to dig further into the plunger.

5. The medical locking device of claim 3, wherein the unlocked position allows the plunger to move axially in and out of the barrel of the syringe.

6. The medical locking device of claim 1, wherein said stop members define the locking and unlocking positions, said unlocked position includes the disengagement of the plunger with the stop members and the locked position includes the engagement of the plunger with the stop members.

7. A medical locking device for securely fitting onto finger grips of a syringe having a longitudinal axis, said locking device being axially aligned with the syringe along said longitudinal axis for receiving a plunger of the syringe, said locking device comprising:

a flat top having a centrally positioned aperture, said aperture for receiving the shaft of the plunger with the shaft of the plunger freely moving axially through said aperture;

retaining members, positioned around said aperture and for receiving securely the finger grips of the syringe by engaging at least three sides of said finger grips, said retaining members eliminating shifting of the medical locking device and positively aligning said centrally positioned aperture;

diametrically opposed cutting means, said cutting means chordally positioned in said centrally located aperture and extending in a plane defined by the flat top, said cutting means tapering into said centrally positioned aperture as a fine cutting edge for wedging into the plunger during execution of a locking condition;

at least two stop members diametrically positioned from each other and fixed at opposite ends of said cutting means, each said stop member extending from said flat top to the other side of said flat top; and said medical locking device securely positioned on the finger grips of the syringe by said retaining means completely engaging the finger grips and allowing the plunger to be twisted in a locking position so that said cutting means wedges into the plunger for eliminating and preventing any further plunger movement in either direction along the longitudinal axis.

8. The medical locking device of claim 7, wherein said cutting means taper with the edges directed upwardly to insure downward motion of the plunger is prevented.

9. The medical locking device of claim 7, wherein said cutting means occupy two positions, a locked position for preventing the plunger from moving axially, and an unlocked position for allowing the plunger to freely move along the defined axis.

10. The medical locking device of claim 9, wherein the locked position forces the cutting edge to dig into the plunger such that any further downward force on the plunger only allows the cutter to dig further into the plunger.

11. The medical locking device of claim 9, wherein the unlocked position allows the plunger to move axially in and out of the barrel of the syringe.

* * * * *